United States Patent
Lancelot et al.

(10) Patent No.: US 6,434,531 B1
(45) Date of Patent: *Aug. 13, 2002

(54) METHOD AND SYSTEM FOR FACILITATING PATIENT CARE PLANS

(75) Inventors: Jean Francois Lancelot; Jon J. Burford; Kristopher S. Urquhart, all of San Diego, CA (US)

(73) Assignee: Clinicomp International, Inc., San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/852,191

(22) Filed: May 6, 1997

Related U.S. Application Data

(63) Continuation-in-part of application No. 08/396,004, filed on Feb. 28, 1995, now abandoned.

(51) Int. Cl.[7] ............................................. G06F 159/00
(52) U.S. Cl. ................................................ 705/3; 705/2
(58) Field of Search ...................... 705/2, 3, 4; 707/10, 707/100–104

(56) References Cited

U.S. PATENT DOCUMENTS

| | | | | |
|---|---|---|---|---|
| 4,878,175 A | * | 10/1989 | Norden-Paul et al. | 364/413.01 |
| 4,893,270 A | * | 1/1990 | Beck et al. | 364/900 |
| 4,987,538 A | * | 1/1991 | Johnson et al. | 364/401 |
| 5,001,630 A | * | 3/1991 | Wiltfong | 364/401 |
| 5,033,009 A | * | 7/1991 | Dubnoff | 364/523 |
| 5,065,315 A | * | 11/1991 | Garcia | 364/413.02 |

(List continued on next page.)

FOREIGN PATENT DOCUMENTS

WO     WO97/15021    *   4/1997

OTHER PUBLICATIONS

Rudisill et al, "Clinical paths for cardiac surgery patients: A multidisciplinary approach to quality improvement outcomes", J Nurs Care Qual 1994;8(3):27–33, Aspen Publishers, Inc., 1994.*

Ashworth et al. "Collaborative Care Documentation by Exception System", Proc Annu Symp Comput Appl Med Care, p. 109–113., PMID: 1482850, UI 93129886, 1992.*

Higgins et al., "A Graphical ICU Workstation", Proc Annu Symp Comput Appl Med Care, p. 783–787, PMID: 1807712, UI: 92222847, 1991.*

M. Ben–Bassat, "Computer Implementation of the Hierarchical–Modulator Approach to Treatment", Methods of Information Medicine, v 21, n 3, pp. 117–126, 1982.*

M. Ben–Bassat, "A Hierarchical Modular Design for Treatement Protocols", Methods of Information Medicine, v 19, n 2, pp. 93–98, 1980.*

Kathleen Healey, "Innovation and Dedication", Hospitals & Health Networks, v 68, n 6, pp. 68–74, Mar. 20, 1994.*

M. Ben–Bassat, "Computer Implementation of the Hierarchical–Modular Approach to Treatment", Methods of Information Medicine, v 21, n 3, pp. 117–126 (abstract), 1982.*

M. Ben–Bassat, "A Hierarchical Modular Design for Treatement Protocols", Methods of Information Medicine, v 19, n 2, pp. 93–98 (abstract), 1980.*

*Primary Examiner*—Frantzy Poinvil
(74) *Attorney, Agent, or Firm*—Foley & Lardner; Bernard L. Kleinke

(57) ABSTRACT

A method and system of facilitating the management of patient care includes storing clinical pathway templates of pre-defined patient care paths, and assigning a template to a given patient undergoing treatment. The assigned template is tailored for the requirements of the given patient, and variances from the patient care path are collected so that the pre-defined patient care path templates can be modified with patient treatment experience.

21 Claims, 7 Drawing Sheets

U.S. PATENT DOCUMENTS

| | | | | |
|---|---|---|---|---|
| 5,072,383 A | * | 12/1991 | Brimm et al. | 364/413.02 |
| 5,077,666 A | * | 12/1991 | Brimm et al. | 364/413.02 |
| 5,121,470 A | * | 6/1992 | Trautman | 395/140 |
| 5,247,611 A | * | 9/1993 | Norden-Paul et al. | 395/161 |
| 5,253,361 A | * | 10/1993 | Thurman et al. | 395/600 |
| 5,253,362 A | * | 10/1993 | Nolan et al. | 395/600 |
| 5,265,010 A | * | 11/1993 | Evans-Paganelli et al. | 364/413.02 |
| 5,301,319 A | * | 4/1994 | Thurman et al. | 395/600 |
| 5,325,293 A | * | 6/1994 | Dorne | 364/413.01 |
| 5,325,478 A | * | 6/1994 | Shelton et al. | 395/148 |
| 5,361,202 A | * | 11/1994 | Doue | 364/413.01 |
| 5,410,704 A | * | 4/1995 | Norden-Paul et al. | 395/700 |
| 5,471,382 A | * | 11/1995 | Tallman et al. | 364/406 |
| 5,473,537 A | * | 12/1995 | Glazer et al. | 364/419.2 |
| 5,517,405 A | * | 5/1996 | McAndrew et al. | 364/401 |
| 5,544,044 A | * | 8/1996 | Leatherman | 364/401 |
| 5,546,580 A | * | 8/1996 | Seliger et al. | 395/600 |
| 5,557,514 A | * | 9/1996 | Seare et al. | 364/401 |
| 5,583,758 A | * | 12/1996 | McIlroy et al. | 395/202 |
| 5,592,945 A | * | 1/1997 | Fiedler | 128/710 |
| 5,594,637 A | * | 1/1997 | Eisenberg et al. | 395/202 |

* cited by examiner

METHOD AND SYSTEM FOR FACILITATING PATIENT CARE PLANS

CROSS-REFERENCE TO RELATED APPLICATIONS

This patent application is a continuation-in-part of U.S. patent application Ser. No. 08/396,004, filed Feb. 28, 1995 now abandoned, entitled METHOD AND SYSTEM FOR FACILITATING PATIENT CARE PLANS, which is incorporated herein by reference as if fully set forth herein.

TECHNICAL FIELD

The present invention relates in general to a method and apparatus for facilitating the implementation of patient care plans in health care facilities. It more particularly relates to a method and apparatus which facilitates the implementation and management of health care plans for patients in a health care facility.

BACKGROUND ART

In modern health care facilities, the care of patients is managed in a cost effective manner. In order to facilitate the managed care, computer systems have been implemented, whereby care plans can be made readily available to the health care providers, such as physicians, nurses and others.

While such systems have proven to be highly successful, for many applications, the initial entry of information into the computer system for the care plan for a particular patient can be time consuming. Since time is of the essence in health care facilities, it would be highly desirable to have a new and improved method and system for facilitating the implementation of patient health care plans.

SUMMARY OF THE INVENTION

Therefore, it is the principal object of the present invention to provide a new and improved method and system for facilitating the management of patient care plans.

Another object of the present invention is to provide such a new and improved method and system, wherein health care providers can more expeditiously and efficiently manage the patient care plans.

A further object of the present invention is to provide such a new and improved method and system for facilitating the management of patient care plans in a more cost effective manner.

Briefly, the above and further objects of the present invention are realized by providing an improved method and system for facilitating the management of patient care plans in a more systematic manner and enabling the plans to be modified with patient experience.

A method and system of facilitating the management of patient care includes storing clinical pathway templates of pre-defined patient care plans, and assigning a template to a given patient undergoing treatment. The assigned template is tailored for the requirements of the given patient, and variances from the patient care plan are collected so that the pre-defined patient care plan templates can be modified with patient treatment experience.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein.

BEST MODE FOR CARRYING OUT THE INVENTION

Figures 1, 1A:
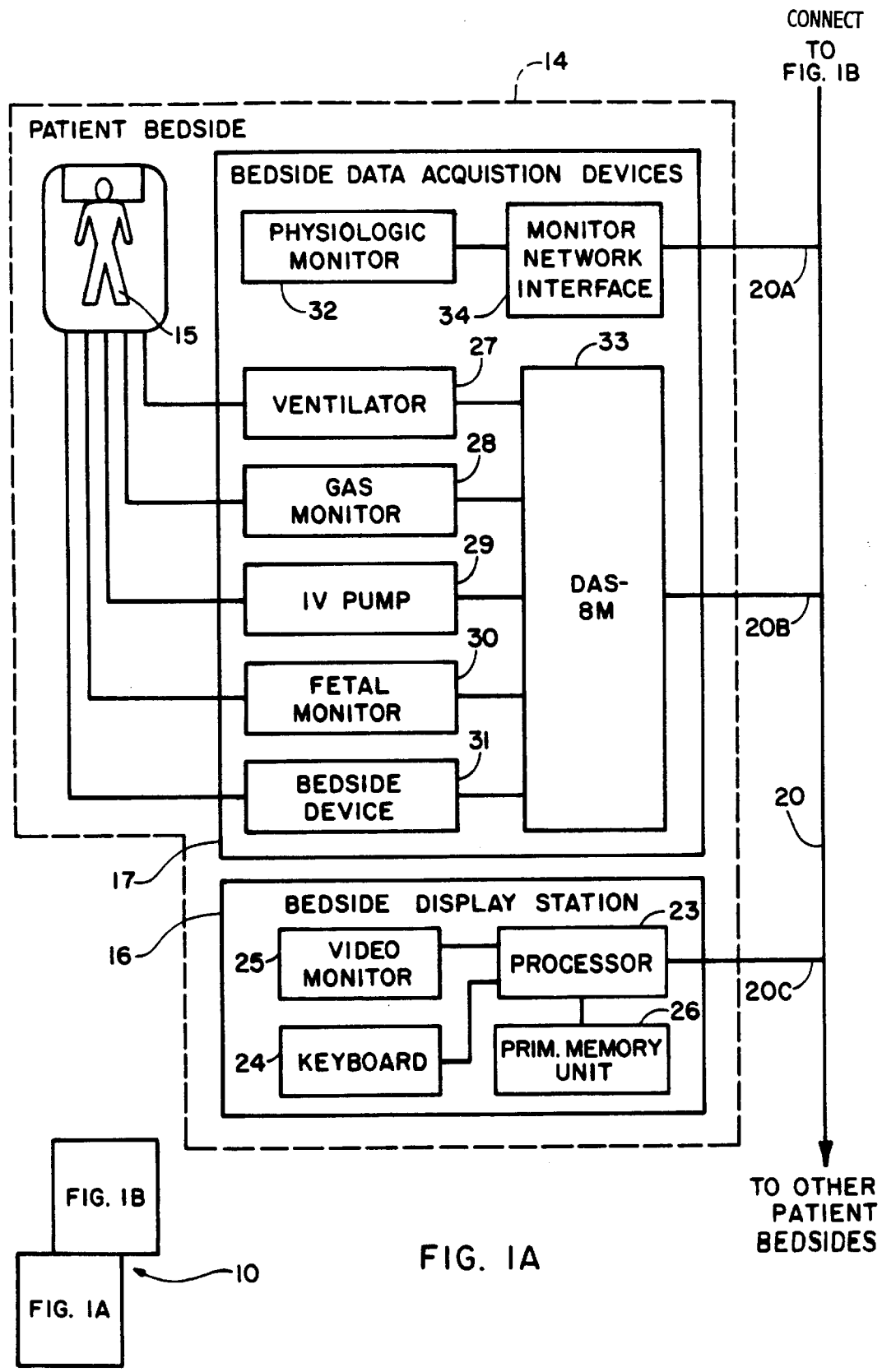
FIGS. 1A and 1B, when arranged as indicated in FIG. 1, is a block diagram of a health care facility arrangement, which is constructed in accordance with the present invention.

Referring now to FIG. 1 of the drawings, there is shown a computerized health care facility arrangement 10, which is constructed in accordance with the present invention and which is adapted to generate automatically patient information including critical care flowsheet information for multiple treatment diagnoses, whether medical, surgical or a combination thereof.

SYSTEM HARDWARE

The arrangement 10 enables a more efficient and effective communication of the patient information among a group of computer systems within the health care facility arrangement 10. In this regard, a group of patient bedside locations, such as a bedside location 14 for a patient 15, is used as an order entry computer system utilized by health care providers such as physicians and nurses to enter the patient information such as clinical orders for the patient 15.

According to the invention, a clinical information system (CIS) 105 (FIG. 2) of the system 10 retrieves patient information such as clinical orders and reformats the retrieved information in object oriented format for sending to one or more of a group of foreign computer systems such as a clinical laboratory computer 15A, a blood gas computer 15B, an A.D.T. computer 15C, a hospital information computer 15D, and other systems 15E such as patient admissions computer, patient billing computer and the like. Each one of the foreign computer systems is equipped with its own application computer software for executing its own specific function.

A clinical pathways administrator (CPA) system 110 (FIG. 2) cooperates with the CIS system 105 to facilitate the management of patient order entries. As will be described hereinafter in greater detail, the CPA 110 helps to control the viewing and entering of patient order entries, and the modification thereof, in a systematic manner.

In short, the arrangement 10 facilitates the monitoring of the standard of care of a large number of patients who are confined at various patient bedside locations, such as the patient 15 located at the bedside location 14. Such an arrangement optimizes delivery of care to patients, enables quicker patient recovery, eliminates undesired and unwanted interventions and achieves a more consistent form of care for each patient in a highly efficient manner. Thus, cost savings are realized for the health care provider and desired results are achieved for the patients.

Although the phrase "critical care path" has been employed, it should be understood that other similar phrases can be used. Such phrases include, but are not limited to: "critical path," "care path," and "care map."

The arrangement 10 generally includes a group of patient bedside monitoring locations located through the facility of a health care provider. Such locations would be in an emergency room, an intensive care unit, a cardiac unit, and so forth.

Each patient bedside location, such as the location 14 includes a bedside display station and a group of bedside data acquisition devices, such as bedside display station 16 and group 17 of bedside data acquisition devices. The display station allows health care providers to observe the patient while entering deviation information at bedside while the data acquisition devices facilitate the gathering of patient data and enable health care providers to monitor the condition of a patient at bedside.

In order to facilitate central monitoring, the arrangement 10 also includes a central computer 12 (FIG. 1B) which communicates individually and selectively with the bedside display stations, such as the display station 16.

The central computer 12 and its associated software gathers and stores patient information, creates flowsheet information, establishes critical care path information for facilitating patient care and to manage the flowsheet information being compiled. The arrangement 10 enables each bedside display station as well as other similar health care provider order entry computers such as a nurse station computer 18, and a physician station computer 19 to access such patient information so health care providers can optimize delivery of care to patients.

The central computer 12 and each bedside patient location display station used for order entry are coupled together via a data bus, such as an ethernet clinical data bus 20. For example, the central computer 12 is coupled to the data bus 20 via a lead or cable 20D, while the bedside display station 16 is coupled to the bus 20 via a lead or cable 20C. In this manner, a health care provider/user can monitor and enter patient information from many different locations.

In order to provide a more fail-safe and secure operation, the system 10 also includes a redundant central computer 13. An off-site support computer 49 is coupled to the data bus 20 via a high speed data link 47 to provide information to remote locations. A report printer 45 is coupled to the data bus 20 via a lead or cable 20F to enable system users to obtain hard copy reports, flowsheets and other documents for providing efficient patient care.

Figure 1B:
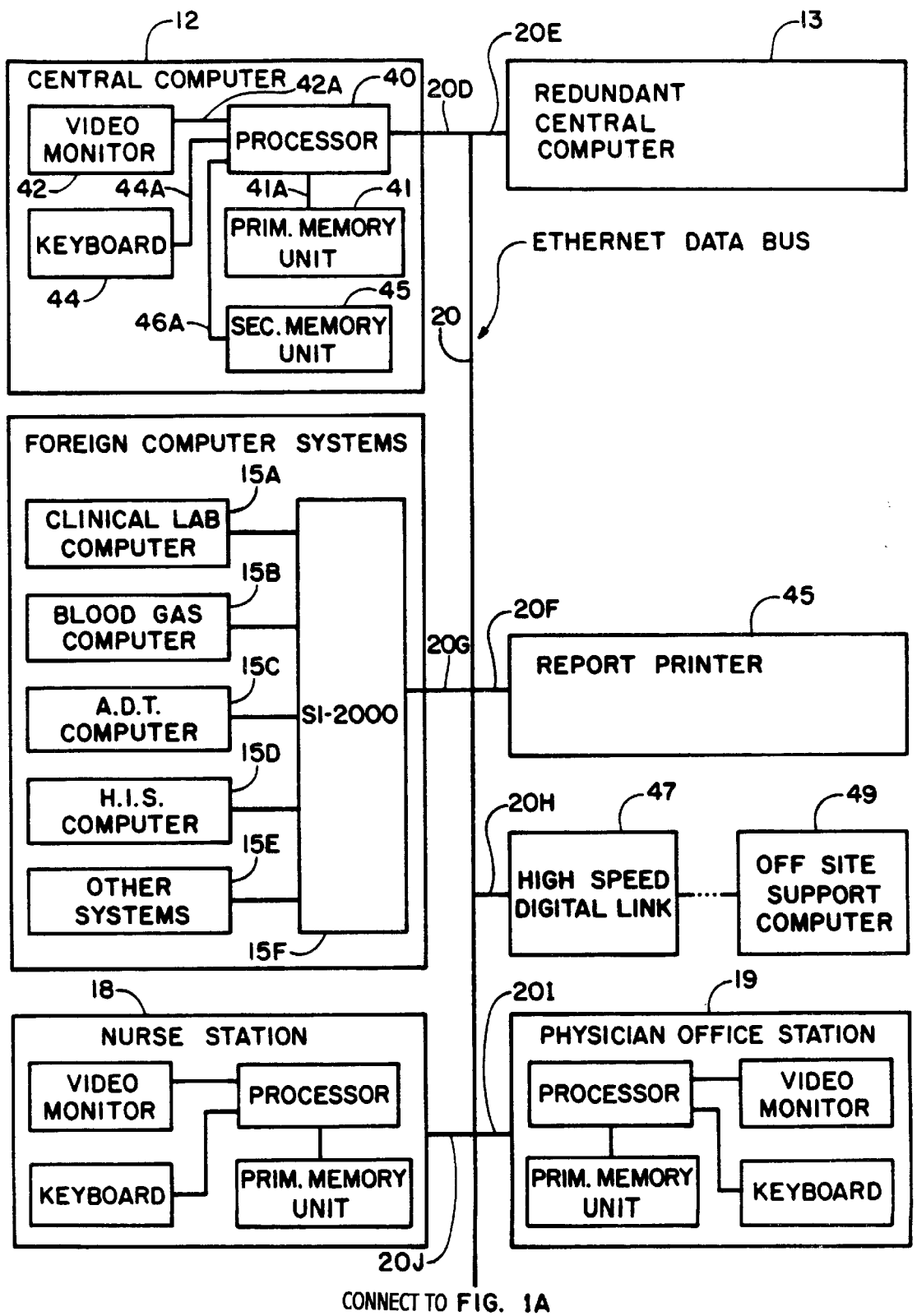

As best seen in FIG. 1B, the redundant computer 13, the nurse station 18, the physician station 19 and the high speed digital link 47 are coupled to the data bus 20 via leads or cables 20E, 20J, 20I and 20H, respectively.

As best seen in FIG. 1A, the group 17 of bedside data acquisition devices includes a ventilator 27, a gas monitor 28, an IV pump 29, a fetal monitor 30, other monitoring devices, such as a special bedside device 31 and a physiologic monitor 32. The devices 27–31 and 32 are coupled to the data bus 20 via a DAS interface 33 having a lead or cable 20B, and monitor network interface 34 having a lead or cable 20A, respectively.

The system 10 via the central computer 12 is coupled to each group of bedside acquisition devices, such as the group 17 of bedside data acquisition devices for the purpose of monitoring each patient in the health care provider facility. In this regard, the central computer 12 gathers information from the data acquisition devices, receives patient information from various health care providers regarding patient orders and patient diagnoses and, in turn, generates customized critical care path information for each patient. The computer 12 stores the gathered patient information, which can be retrieved by an object request broker computer in response to a request message from one of the foreign computers.

As more fully described in the foregoing mentioned co-pending U.S. patent application, the customized critical care path information is, in turn, utilized by the computer 12 to manage the compiling of flowsheet information for each patient. The flowsheet information is an ongoing compilation of patient information for each patient.

For example, with respect to the group 17 of bedside data acquisition devices, those skilled in the art will understand that as each patient requires customized care, certain ones of the monitoring devices may not be required. Also, which interface device or devices are required, such as the devices 33 and 34, depends on the type of data acquisition devices utilized for monitoring a patient, such as the patient 15. Thus, in accordance with the customized patient information, the arrangement 10 determines that certain rows of the flowsheet may be unnecessary to cause them to be unused whenever it is determined that a certain bedside data acquisition device is not required for a certain patient. In short then, the critical care path patient information is used by the central computer 12 to manage the flowsheet information causing it to be appropriately compiled for each particular patient being monitored by the arrangement 10. In this manner, a more consistent form of care for each patient is facilitated in a highly efficient process.

Considering now the central computer 12 in greater detail with reference to FIG. 1B, the central computer 12, includes a processor 40 having coupled thereto a primary memory unit 41, such as a random access memory unit, a monitor 42, a keyboard 44 and a secondary memory unit 46, such as a disc drive memory unit. The central computer 12 is generally a super mini-computer, such as sold by Digital Equipment Corporation, Inc. and others. The computer processor 40 is interconnected to the memory unit 41 via a memory cable 41A, the monitor 42 via a video cable 42A, the keyboard 44 via a keyboard cable 44A, and the secondary memory unit 46 via a memory post cable 46A. The primary memory unit 41 and the secondary memory unit 46 contain the long term database information for the critical care path system, and the application software to receive patient data from the bedside display station 16.

The processor 40 and its associated application software performs all the necessary functions of critical care path patient information including 1) retaining clinical information for retrieval and review;. 2) performing requested clinical calculations; 3) displaying patient data in tabular and graphic formats; 4) allowing simultaneous multiple user access to any given patient chart information; and 5) integrating patient data acquired from the bedside data acquisition terminals and other acquisition systems such as a clinical laboratory information computer system 15A, a blood gas laboratory computer information system 15B, an A.D.T. (admissions discharges and transfers) computer information system 15C, an H.I.S. (hospital information system) information system 15D, and other foreign systems, such as a foreign computer system 15E.

As best seen in FIG. 1B, an interface unit, such as an SI2000 interface unit 15F, enables such other systems 15A–15E to be coupled to the data bus 20 shared by the central computer 12, the redundant computer 13, and the off-site support computer 49.

Considering now the bedside display station 16 in greater detail with reference to FIG. 1A, the bedside station 16 includes a central processor 23, keyboard 24, video monitor 25 and a primary memory unit 26 such as a random access memory unit. The display station 16 is disposed at the patient bedside location 14 so the health care provider can be in close contact with the patient as information regarding the condition of the patient is entered into the system 10.

The redundant central computer 13 is substantially similar to the central computer 12, and will not be described in greater detail. Those skilled in the art, however, will understand that all of the functions performed by the central computer 12 can also be performed by the redundant computer 13, as well as any other computer system coupled to the data bus 20 having sufficient speed and secondary memory capability. In this regard, the system 10 has a redundant capability.

SYSTEM OPERATION

As noted earlier, the arrangement 10 is a hardware and software system that facilitates the communication of patient information among computer systems. In this regard, the arrangement 10 operates under a master or main program that starts whenever the central computer 12 is activated. In this regard, the arrangement 10 is adapted to be active or ON at all times, since critical care path patient information typically requires twenty-four hour per day, seven day per week monitoring. As all of the system stations can operate independently and simultaneously using the same application software, only the operation of the central computer 12 will be discussed. For clarity purposes in understanding the operation of the arrangement 10, reference may be made from time to time to other stations or data acquisition units.

In operation, and by way of example, consider a patient admitted to a health care facility for a surgical hip replacement procedure. A designated health care provider user utilizing the arrangement 10 via the physician station 19 enters the patients name, the surgical diagnosis and any special orders. The entered information is transferred via the lead or cable 20I to the data bus 20 and thence lead or cable 20D to the central computer 12.

The central computer 12 via the processor 40 causes the information to be processed and stored in the secondary memory unit 46 via the memory port lead 46A. In this regard, the central computer 12 retrieves selectively under user control, critical care path patient information.

After the health care provider/user has tailored the critical care path patient information, the user can cause the information to be stored in the secondary memory unit 46, for subsequent access by support personnel at the bedside of the patient via a display station, such as the display station 16. Such information may also be accessed by the nurse station 18 and the physician office station 19.

When the central computer 12 receives the tailored or customized patient information, the central computer 12 causes customized patient information to be compiled based upon the critical care path information. In this regard, flowsheet information including clinical orders is initially stored in a universal format for displaying many possible patient management information received from the display station 16 and the group 17 of bedside data acquisition devices.

After the patient is at bedside, patient information is gathered by the health care provider/user via the display station 16, and the appropriate bedside devices and then stored in the central computer secondary memory unit 46 for subsequent retrieval by one of the foreign computers in accordance with the present invention. In this regard, the ethernet data bus 20 has common access to each of the systems, computers, and devices via the leads or cables 20A–D and G.

More particularly, a health care provider user or a user of a foreign computer at any time thereafter, can access the stored patient information stored at the central computer 12 via the bedside display station 16, the nurse station 18, and the physician office station 19, as well as via a foreign computer.

From the foregoing, it should be understood that the arrangement 10 facilitates the management of the care of a large group of patients. The management of care is accomplished by creating and storing in the secondary memory unit 46 of central computer 12, patient information including clinical orders, for a large number of different patient diagnoses, both medical and surgical.

SYSTEM SOFTWARE ARRANGEMENT

Figure 2:
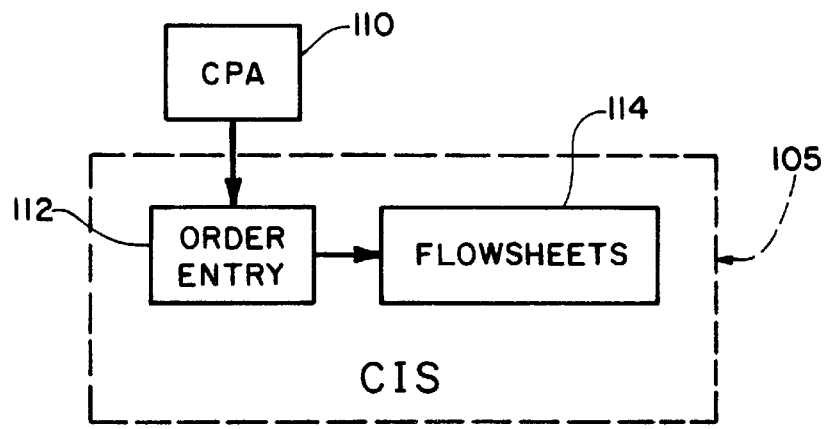
FIG. 2 is a block diagram of a patient order entry arrangement for the health care facility arrangement of FIGS. 1A and 1B.

Considering now the system software arrangement for the system 10 with reference to FIG. 2, the CPA 110 will sit "on top of" the CIS 105 and provide a way to view and manage order entry in a controlled fashion according to medical facility protocol. The CPA 110 will communicate (indirectly) with the CIS 105 via the existing order entry application 112, effectively replacing standard order sets. A flowsheets application 114 is responsive to the order entry application 112.

The CPA 110 is accessed via a CIS hardkey (not shown), similar to current CIS 105 applications. Using the various functions of the CPA 110, described below, orders will be stored to the patient's CIS database. The resulting orders are identical to the patient orders described in the aforementioned copending U.S. patent application, and are used in the exact same manner.

The end user of the CIS 105 will not be directly affected by the CPA 110. The actual care giver need not know whether or not a given patient is on a clinical pathway. The CPA 110 is utilized at a higher administrative level by the personnel responsible for making clinical decisions, i.e. physicians and therapists.

It is assumed that the user of the CPA exhibits the following characteristics: is responsible for decisions relating to the clinical care of the patient; and is sufficiently computer literate to operate a pointing device oriented graphical user interface.

Use of the CPA 110 requires the following: the users must be trained in the operation of the CPA 110; and the site must develop and maintain Pathway templates using CPA configuration mode, as will be described hereinafter in greater detail.

The concept of time is important to the understanding of the CPA 110 operation. Time is divided into two regions: the past to the left and the future to the right. Between the two regions of past and future is an instant in time referred to as the present.

Every object in the CPA 110 to the left of current time is considered to be in the past. Under normal operation, the editing of items in the past is not required, but will be allowed. Edited items are visually indicated. The deleting of objects in the past that create CIS data objects (e.g. approved orders) is not allowed.

Current time corresponds to the current clock time, with a minimum resolution of about one minute. As time passes, the current time will be continually updated, with time and objects scrolling to the left.

Objects to the right of current time are considered to be in the future. All future objects can be edited, new objects can be added, and existing objects can be deleted.

A level is the major conceptual building block for the CPA 110. The level contains three essential parts that are very tightly interconnected, and contains a group of related orders. When the level is "started," these orders are stored to the patient's CIS database and will be accessible via the CIS order entry facility. The orders will be stored according to the ENT/APP/CS permissions of the current user. Once started, the left edge of the level will begin to scroll to the left since it is now in the past.

The level contains an expected duration corresponding to a "width" along the timeline. The expected stop time of the level is equal to the actual start time of the level plus the expected duration. As time passes, the stop time scrolls from right to left until it hits current time. If the level is not stopped at this point, the duration of the level will increase to make the level wider.

The level also contains an expected outcome. This outcome must be met for the level to be stopped. Once the expected outcome is met, the level is stopped, and the level's orders are discontinued at current time. At this point, the entire level is in the past.

Configuration made allows medical facility designated personnel to create, modify, and delete non-patient specific Pathway templates for future use by the administration mode. Security features restrict access to the configuration mode of the CPA 110.

The configuration mode allows the user to: configure individual orders; group orders into levels; group levels into rows; group rows into sections; and group sections into a Pathway. The configuration of Pathway templates is environmentalized to accommodate the differences in protocols between units within the medical facility.

An administration mode is the normal operation mode of the CPA 110. The administration mode provides the ability to add a template to a patient's clinical pathway. This template can be customized to fit the clinical needs of the patient. Multiple templates can be added and merged with the existing clinical pathways at any point during the lifetime of the clinical pathway.

In addition to entire Pathway templates, individual preconfigured sections, rows, levels, and orders can be added at any time to the current and/or future portion of the CPA 110, in whole or in part (e.g. path in progress).

Once the templates and individual objects are added to the patient's clinical pathway, the CPA 110 can be used to store and discontinue orders as described above.

All objects in a pathway can be annotated in a fashion similar to flowsheet items in the CIS 105. These annotations will be visually indicated on the Pathway and will also be viewable from the CIS Note Menu.

A note can be associated with every object in the Pathway. This allows configurable and queryable object-specific data to be charted (e.g. teaching notes). Notes are charted as CIS Notes, and as such will be configurable by the medical facility as to their contents and layout. This will also enable notes to be viewed via the CIS Note Menu, similar to annotations.

One of the main goals of the CPA 110 is to permit the evolution of a Pathway template based on clinical data. For example, if the expected duration of a level is initially 8 hours, but a majority of patients actually require 10 hours, the expected durations should be changed to 10 hours.

To facilitate this kind of evolution, variances of duration will be detected automatically by the CPA 110. The user will be required to classify the variance. Statistics regarding the actual duration of levels will be automatically gathered by the CPA 110 for use by the configuration personnel. A variance of duration can be either positive or negative.

In addition to variances of duration, there may be other types of variances that can be detected. For example, if a level template contains four individual orders, but one of the orders is routinely deleted on the actual pathway, this order can be deleted from the template.

Variances will be charted as CIS Notes, and as such will be configurable by the medical facility as to their contents and layout. This permits the variances to be viewed via the CIS Note Menu, similar to annotations.

Figure 3:
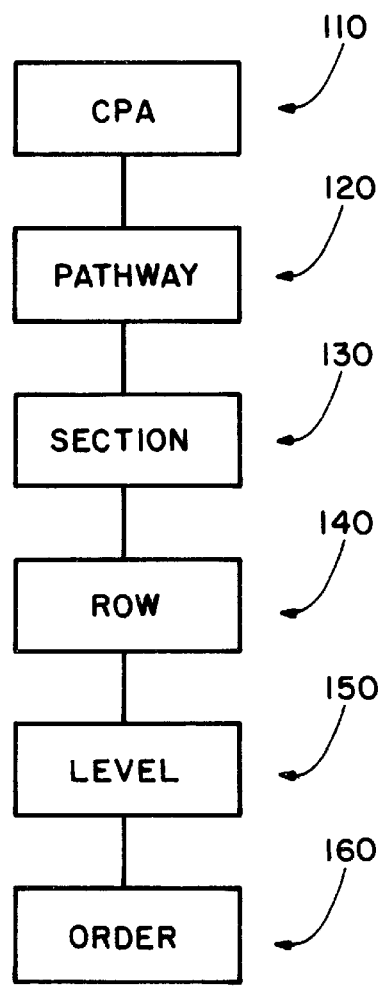
FIG. 3 is a block diagram of a hierarchical arrangement of objects.

The CPA user interface includes objects that are related in a hierarchial fashion. With reference to FIG. 3, a particular object is made up of a collection of zero or more occurrences of the object directly beneath it in the hierarchy (children objects). All objects have most characteristics in common with the other objects, along with some characteristics that are unique to a particular object. The common features are described in the first subsection, followed by the object-specific characteristics.

An object optionally contains: a text field of unlimited length; annotations (max one per minute); a note; variances (max one per minute); and a group of related children objects.

An object can: display its contents in both a verbose and an abbreviated format (e.g. just the name), and provide a means for toggling between the formats; be horizontally and/or vertically resizeable; be horizontally and/or vertically scrollable; and provide a means to activate variance tracking on the CIS 105.

An object supports the following operations on children objects: add and delete; start and stop; and copy and paste.

In addition to the common object characteristics, an order 160 contains: generic order data (e.g. type, category, name, start time, stop time); and any type specific data (e.g. schedule, dose, comment, etc.).

The order 160 can: provide a means for editing the contents of an unapproved order; provide a means for approving and/or countersigning an order; and provide a means for changing the start time of an unapproved order.

In addition to the common object characteristics, a level 150 contains: an expected outcome including a text string describing the conditions that must be met for the level to be considered complete; and an expected duration (e.g. 8 hours).

A level can: provide a means for editing the expected outcome; and provide a means for editing the expected duration. In particular, only the level's end time can change. It can be made to end earlier or later.

A row 140 exhibits the common object characteristics.

A section 130 exhibits only the common object characteristics.

A Pathway 120 exhibits only the common object characteristics.

The CPA 110 exhibits only the common object characteristics.

The CPA user interface is a graphical user interface that supports, but does not require, the use of a pointing device. The CPA user interface is more sophisticated than the CIS user interface. For example, the CPA user interface includes push-buttons, pulldown menus, pop up windows, and other features common to state of the art graphical user interfaces.

A typical Pathway 120 contains a large volume of information. It is impractical to display all of the information at any given time.

As mentioned above, the horizontal axis of the screen will represent time, with the past to the left and the future to the right. The screen by default will have current time in the middle of the screen, but the screen can be scrolled both left and right to see what happened in the past and what may happen in the future.

Rows are distributed vertically, optionally organized into sections of related rows. Vertical scrolling will allow the user to view different sections of the Pathway 120 for a given time frame.

Zooming allows the user to change the magnification factor and/or the level of detail displayed. Thus, it will be possible to see an entire multi-day Pathway 120 on the screen at one time, but the individual orders may not be visible.

The use of color enhances the usability and visual appearance of the CPA 110. For example, variances and/or annotations may be visually indicated using color, which takes up no screen space in and of itself. While color displays will provide the best results, shading can be used to simulate color on monochrome displays.

In addition to the orders and tasklist printing features of the existing CIS 105 (FIG. 2), the CPA 110 will provide printing of both Pathway templates and individual patient's Pathways. Entire Pathways may be printed at one time, or just a specified portion. For example, only a certain time span, and/or only certain sections or rows could be specified. In addition, it is possible to specify the level of detail to print.

The CPA 110 is not dependent on any other software product for operation. It operates directly on a patient's database by retrieving and storing unapproved orders. This achieves an indirect communication with the CIS 105. Database consistency, redundancy, and auditing is achieved by utilizing the CIS database library routines.

The CPA 110 shall: support any number of simultaneous users on any number of redundant hosts; and provide asynchronous update of any changes made from another terminal.

The CPA 110 shall remain available to the user at all times. In particular, the CPA 110 will not restart silently. The user will be advised of any internal problems before restart.

The graphical user interface is implemented to facilitate an easy move to another graphical user interface should the need arise.

The CPA 110 is highly portable, as: less than 5% of the components will be host-dependent; less than 2% of the code will be host-dependent; a proven portable language will be used (e.g. C or C++); and all code will be compatible with the UNIX operating system (SVR2 and up).

SYSTEM SOFTWARE OPERATION

Figure 4:
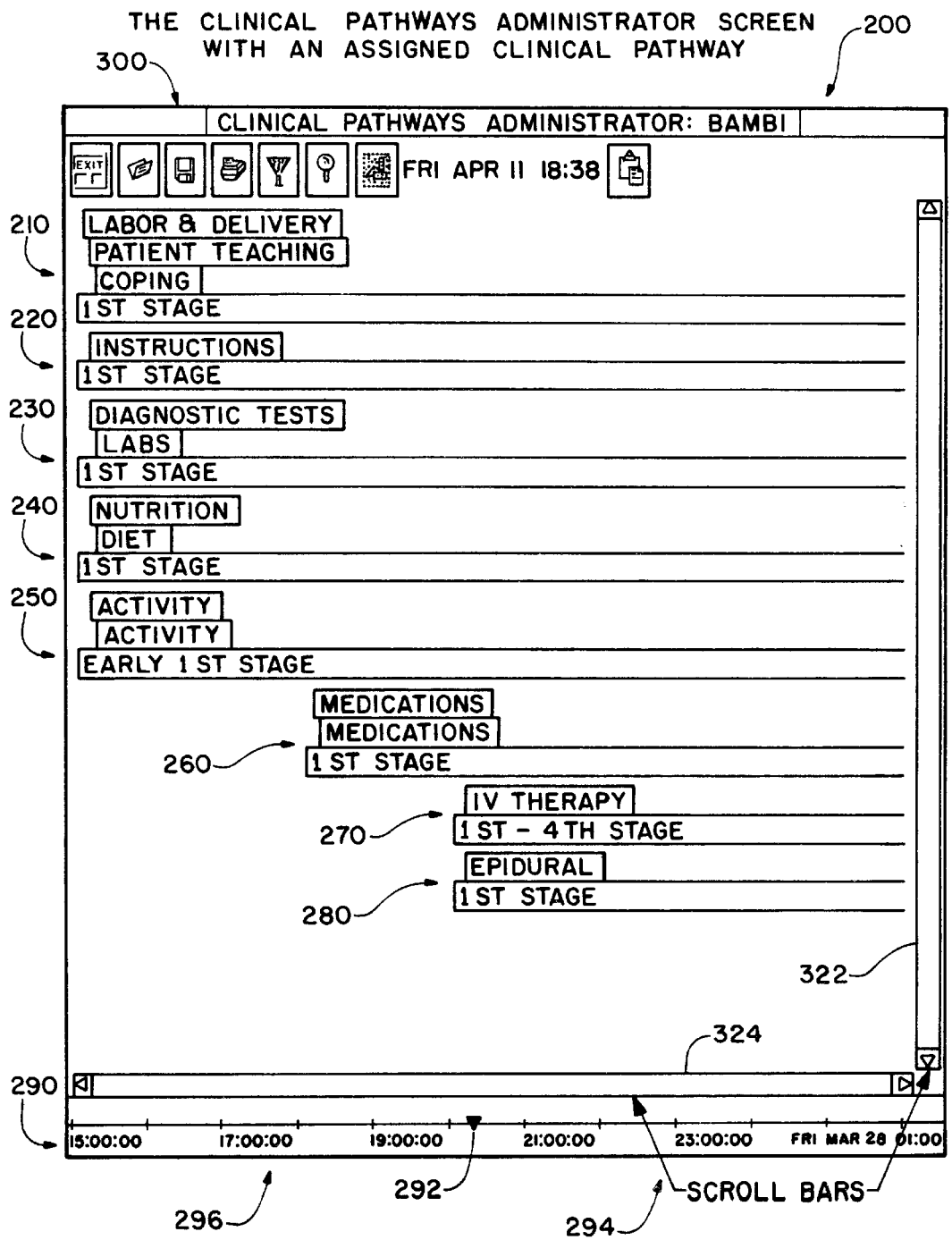
FIG. 4 is a view of a clinical pathways administrator screen, with an assigned clinical pathway.
Figure 5:
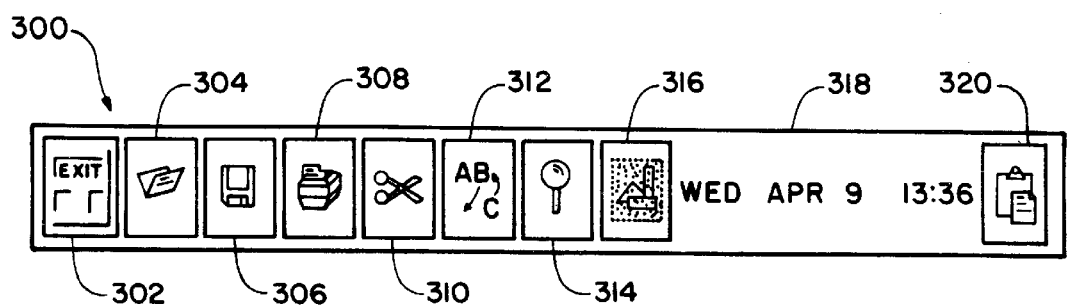
FIG. 5 is an enlarged view of a tool bar from the screen of FIG. 4.

Referring now to FIGS. 4–11, the CPA 110 (FIG. 2) enables the user to access patient order information with a clinical pathway administrator screen, such as screen 200 (FIG. 4).

The Clinical Pathway Administrator Screen 200 is accessed by selecting an appropriate key sequence for the Clinical pathway Administrator Screen. Upon accessing the Clinical Pathway Administrator Screen 200 a Tool Bar 300 including a grouping of icons appears in the upper corner of the screen. When a cursor (not shown) is placed above an icon, its functional will be described in text below the icon. The icons from left to right are: Exit 302, Open 304, Save 306, Print 308, Filter 310, Zoom 312, Configuration Mode 314 and Clipboard 316.

When the Exit icon 302 is selected, the Clinical Pathways Administrator screen 200 is exited. When the Save Icon 306 is selected, any changes to the screen 200 are saved.

More than one clinical pathway can be assigned to a patient and displayed on the screen 200. To assign a clinical pathway to a patient, the "Open" 304 icon is initially activated. A current Pathways window appears. The Available pathways are existing templates for that environment that can be selected and tailored as needed for the patient. The Patient's pathways are pathways that have been assigned to the patient.

The desired pathway is selected from "Available Pathway" option by activating the OK button (not shown). To prevent the storage of any unstored orders to the pathway, click on a "Cancel" button (not shown) is activated. The details of a pathway that will be displayed on the screen 200 is configurable per the environment.

A Clinical Pathway is a diagnosis specific, multi-disciplinary time-sequenced patient care plan. The Clinical Pathway is started for each patient by assigning a pathway template that has been defined by the hospital per existing Standards of Care. The pathway can be tailored based on the patient's expected outcomes. Orders added to the patient's pathway will be automatically transferred to the appropriate flowsheet and appear on the Order Entry Screen. A clinician can chart whether the pathway's outcomes were met (completed) or if a variance occurred. Variances may be user-defined or global and are initiated individually or automatically.

Figure 6:
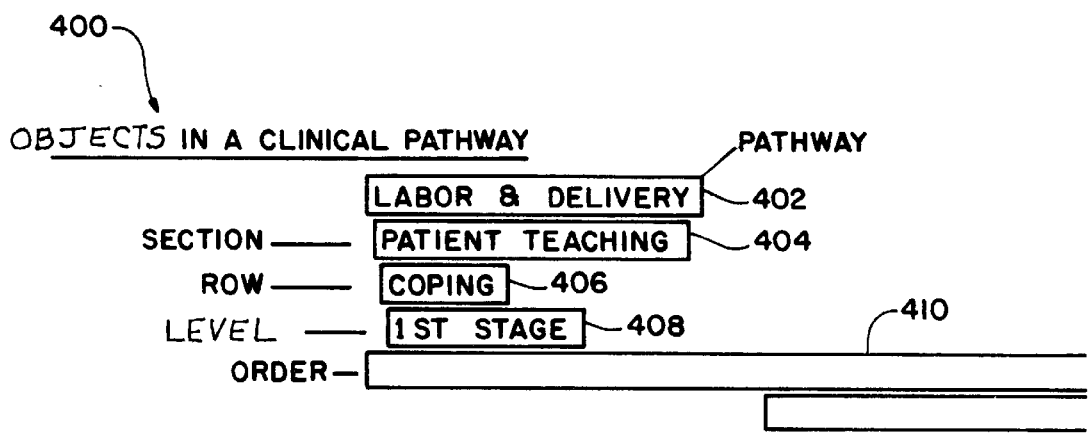
FIG. 6 is an enlarged view illustrating levels of a pathway.

Considering now the levels of the CPA 110 in greater detail with reference to FIG. 6, the Clinical Pathways Administrator Screen 200 (FIG. 4) is divided into levels in which the first level is the Pathway and subsequent levels are the components of the pathway. Each pathway can contain one or more of the following levels: pathway; section; row; step; and order.

A top level is defined as a Parent and a subsequent level is defined as a Child of the Parent level. Each parent level is represented on the screen by a unique color. Each level is labeled, enclosed within a box, and visibly indented from the previous level.

The levels, in hierarchical order, include:

a) Pathways Level 402—More than one clinical pathway can be shown for a patient. Typically, when a pathway is selected, only the pathway will be visible on the screen.

b) Section Level 404—A section is a child to the clinical pathway 402. Sections on a clinical pathway may be used to separate different types of charting parameters (i.e. Diagnostic Tests, Diet, Activity).

c) Row Level 406—A Row is a child to the Section 404. Rows may be used to separate the charting parameters (i.e., Labs, Radiology, etc.).

d) Step Level 408—A Step is a child to a Row 406. Steps are configured to show an interval of time such as a Phase, a Day, a Stage, etc. Steps for one row are displayed next to each other to visually show the new time interval.

e) Order Level 410—A order is a child to a Level 408. Orders are assigned via access to the Order Screen and the name of the order appears in the box representing an order.

The following definitions describe various features of the CPA 105.

Active Clinical Pathway—a pathway where the current time falls between the start and end time of any level within a pathway. Any changes to an active pathway will generate a variance, but discontinuing an expected time will not generate a variance.

Inactive Clinical Pathway—Saving a pathway as inactive.

User Mode—enables patient order information to be accessed.

Configuration Mode—enables the CPA 105 interface to be adjusted.

Current time—is equal to the current clock time with a minimum resolution of one minute. As time passes, the current time will be continually updated and the time and pathways will scroll to the left.

Level Box—is the box encircling the label and time duration of a level. The Left edge of the box indicates the level's start time. The Right edge of the level box indicates the end time of the level.

Annotation—is distinguished by an Asterisk (*) and describes any notable event.

Variance—is distinguished by a dollar sign ($) and describes any change to a pathway.

Figure 7:
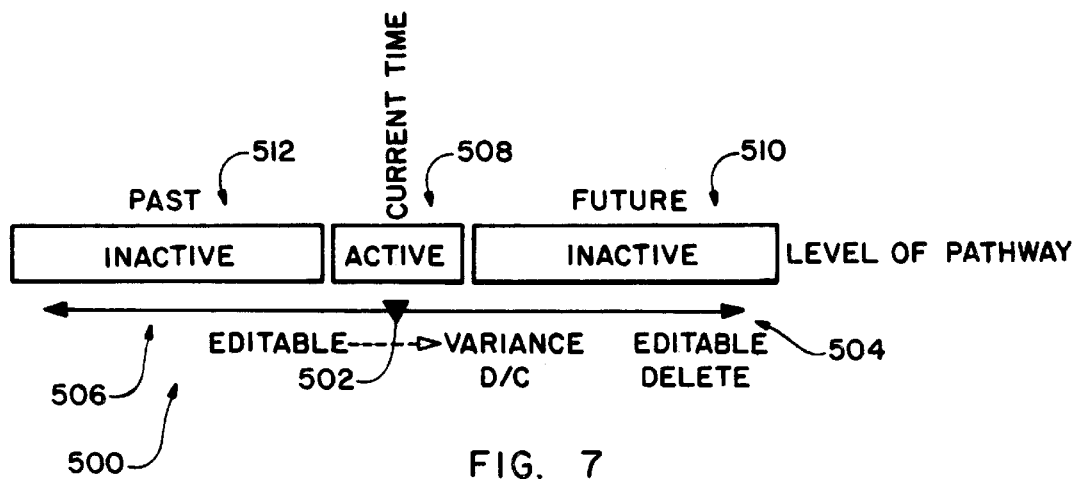
FIG. 7 is a diagrammatic view of the representation of time for a pathway.
Figure 8:
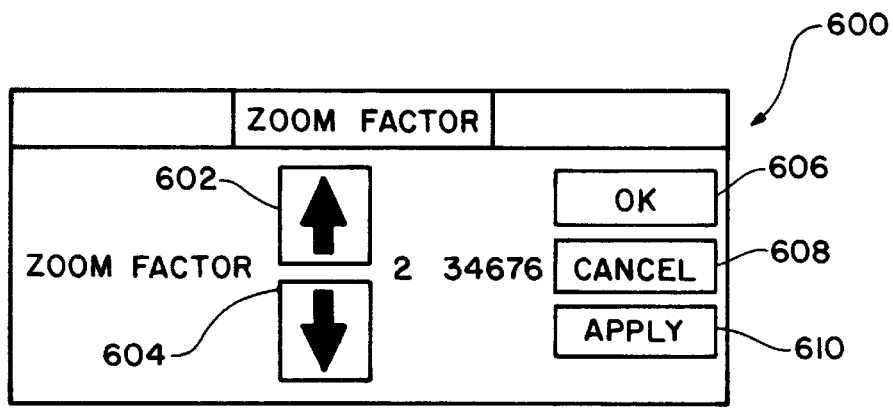
FIG. 8 is an enlarged view of a zoom factor window.
Figure 9:
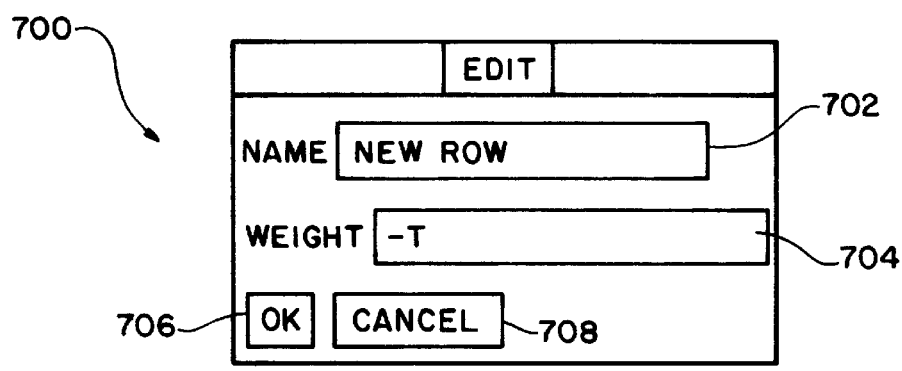
FIG. 9 is an enlarged view of an edit window.
Figure 10:
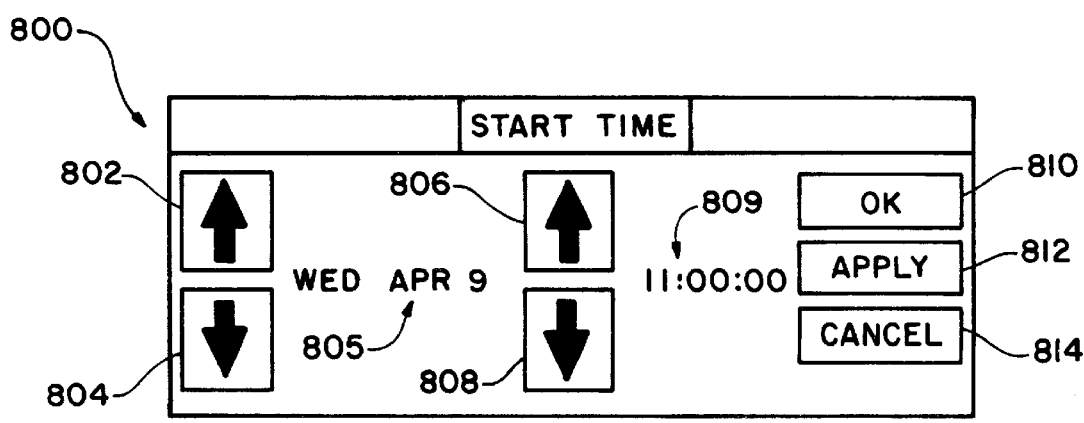
FIG. 10 is an enlarged view of a time window.

Considering now the concept of time as used by the CPA 110 with reference to FIG. 7, the pathway 502 is displayed over time. The current time 508 is indicted at the bottom of the screen by an upside down arrow. The time 512 to the left of current time is the past; the time 510 to the right of the current time is the future.

The Clinical Pathway can be viewed in number of various formats. For example, to expand a parent level, the right mouse button is held down and a child level is selected. The lower the child level, the more children levels will appear. To close a level, the right mouse button is held down and the level is selected again.

The screen can be scaled to better view the patient's pathways. To change the display size of a pathway, a zoom factor window 600 provides a quick tool for controlling the display size. Clicking on the zoom button 308 on the tool bar 300 of FIGS. 2 and 3 causes the Zoom Factor window 600 to appear.

To increase or decrease the zoom factor, up arrow 602 and down arrow 604 are activated as desired. To save the new display size, click on the "OK" button 606.

To locate all orders of a particular order type (i.e., Treatments, Medications, etc.), the "Filter" icon 310 (FIGS. 2 & 3) is activated to cause a Filter Order window (not shown) to appear.

One or more order types can be selected from the Filter Order window. Once a desired order type is selected, an "OK" button (not shown) is activated.

Those levels in a pathway that contain the filter order types will appear on the screen.

To return the display of the pathway to all order types, deselect all selected order types in the Filter Orders window.

To view an order, the cursor is moved to the desired order. The right mouse button is held down, and the View Order option is selected.

The Order Screen will now appear and the order may be viewed. When completed with viewing the order, the "Exit" button is activated.

To configure a Clinical Pathway for a patient, the patient's pathway is initially stored as inactive.

A new level can be quickly created or moved by copying and pasting a similar level. To create or move a level, the cursor is moved to the level to be copied. The middle mouse button is held down, wherein the cursor changes to the Copy icon. The Copy icon will take on the color for that level.

To copy a level, the Copy icon is dragged to the desired parent level or pasted to the Clipboard at the top of the screen for later pasting. For example, when creating a new Row, a desired Row is selected and the Copy cursor is held down and dragged to the Section level in which the new row will reside. The middle mouse button is then released. The level will appear under the selected level or in the Clipboard icon. Children levels will not be visible and will need to be expanded.

When a parent level is deleted, the children levels will also be removed. To remove a level off a pathway template, the cursor is moved to the desired level. The right mouse button is held down, and the Delete option is activated. As a result, the level will be removed from the pathway.

A pathway cannot be deleted.

To change the name of a level, the cursor is moved to the desired level. The right mouse button is held down and the Edit option is selected.

By selecting the Edit option, an Edit window 700 will appear with the fields available for editing per the level selected. A name field 702 is activated to select the name to be edited. The name is then edited as desired and an "OK" button 706 is clicked to indicate the name is correct. The name of the level will appear as the edited text.

To assign the importance of a level with a value, the cursor is moved to the desired level. The right mouse button is held down and the Edit option is activated. The Edit window 700 will appear.

A weight field 704 is activated to select the desired weight for the level. After entering the desired weight, the OK button 706 is clicked.

Orders are not assigned a weight.

To create a new order, the cursor is moved to the Parent Step level where the New Order will reside. The right mouse button is held down and the New Order option is clicked. A New Order will appear in the Step. Another order can then be selected, dragged to the desired order position, and dropped.

Where an order is discontinued outside the expected time configured time window, a variance will be automatically generated. Whenever an order is deleted in the user mode, a variance is automatically generated. To discontinue or delete an order, the cursor is moved to the order to be discontinued or deleted. The right mouse button is held down and either the discontinue (D/C) or Delete option is activated.

An "OK" button is then activated, and a D/C Time window appears. The desired D/C time is entered. If the D/C time is within the configuration time window of the expected time, the order will be discontinued.

If the D/C time is outside of the configuration time window of the expected time, then the Notes Menu screen will appear for the entry of a variance. The Notes Menu screen will appear for the entry of a variance Note.

The Start Time for an order can be assigned via the Edit function or by dragging the order box while holding down the Left Mouse button.

To assign the Start Time for a pathway, section, row, step, or order, the cursor is moved to the desired level. The right mouse button is held down and the time option is activated.

A Time window 800 appears when creating a start time or when changing the start time. The time window 800 allows the day and the time in hours to be modified. The window 800 includes up arrows 802 and 806 and down arrows 804 and 808 to increase or decrease the day and time for the start time.

The "Up Arrow" button 800 adds a day to the date and the up arrow button 806 adds an hour to the time. The "Down Arrow" button 804 subtracts a day from the date and the down arrow button 808 subtracts an hour from the time. The "OK" button 810 is activated when the desired time is selected.

For an order only, the cursor is moved over the desired edge of the level box to be changed. The Left mouse button is held down and the level box is dragged to the desired time. The Left mouse button is released when at the desired time.

Once a pathway has been assigned for a patient, the user can then: chart an annotation on the patient's status; or record the outcome for a level has been met; or adjust the pathway per the patient's status.

The note circumstances surrounding a patient's status on a clinical pathway, the cursor is moved to the desired level. The right mouse button is held down and a Chart Annotation option is activated. The Notes Menu for entering an annotation will appear.

The desired note is selected and the Note Time window will appear. If the note is a timed note and the pathway already contains one, a prompt will appear to select another note.

The time is then entered and the selected note appears. The requested note information can then be entered. When completed with entering the note, the "Store" soft key <F8> is activated. A user ID code is then entered. To return to the Clinical Pathway Administrator Screen, the "Exit Note" soft key <F1> is activated.

To view any annotation on a patient's clinical pathway, the cursor is moved to the desired level. The right mouse button is held down and the View Annotations option is activated. The Notes Menu screen will appear with a patient's annotations displayed for the selected level only.

To view an annotation, the "Review Note" soft key <F2> is activated.

When the outcomes for a patient have been met, the clinician can record the completion and discontinue the level. By selecting the Outcome function for a level, the user can view the expected outcome with the option to discontinue the level.

To record the completion of a level's outcome, the cursor is moved to the desired level. The right mouse button is held down and an Outcome option is activated. A list of outcomes will appear in the Outcomes window.

Where the listed outcome was accomplished, a "Complete" button is activated. A D/C Confirmation prompt will appear. Selecting an "OK" button causes a D/C Time window to appear. The desired D/C Time for a single level can then be entered.

Any change to an active pathway requires the clinician to chart a variance. The type (i.e., individual, global, etc.) of variance charted by the clinician depends upon the Variance Note selected. The health care facility is responsible for configuring variance notes for individual, globular non-discoverable (i.e., variances not stored to patient record) incidents.

To chart a variance, the cursor is moved to the desired level. The right mouse button is held down and the Chart Variance option is activated. A Variance Note menu will appear.

The desired variance note is activated and a Note Time window appears. If the note is a timed note and the pathway already contains one, a prompt will appear to select another note.

The time is entered to cause the selected variance note to appear. When completed with entering the variance note, the "Store" soft key <F8> is activated.

The user ID code is entered and the Clinical Pathway Administrator Screen returns by activating the "Exit Notes" soft key <F1>.

To view the variances on a patient's clinical pathway, the cursor is moved to the desired level. The right mouse button is held down and the view Variances option is activated. The Notes Menu screen will appear with a patient's variances displayed for the selected level only.

To view an annotation, the "Review Note" soft key <F2> is selected.

When completed with viewing an patient's annotation, the "Exit" <F1> is activated.

Editing an Active path will automatically generate a variance.

To discontinue a level, the cursor is moved to the desired level. The right mouse button is held down and the discontinue (D/C) option is activated. A D/C Confirmation prompt will appear.

Activating the "OK" button will cause a D/C Time window to appear. The desired D/C time is then entered. The Notes Menu for entering a variance will appear, and a variance can be entered.

When the patient status completes the outcome for a Step, the step can then be discontinued via the complete option. Completing a step allows the clinician to quickly discontinue all the orders in a step at one time without viewing the outcomes.

To complete a Step, the cursor is moved to the desired level. The right mouse button is held down and the Complete option is activated. A D/C Confirmation prompt will appear.

Activating the "OK" button causes the D/C time window to appear. The desired D/C Time can then be entered.

Figure 11:
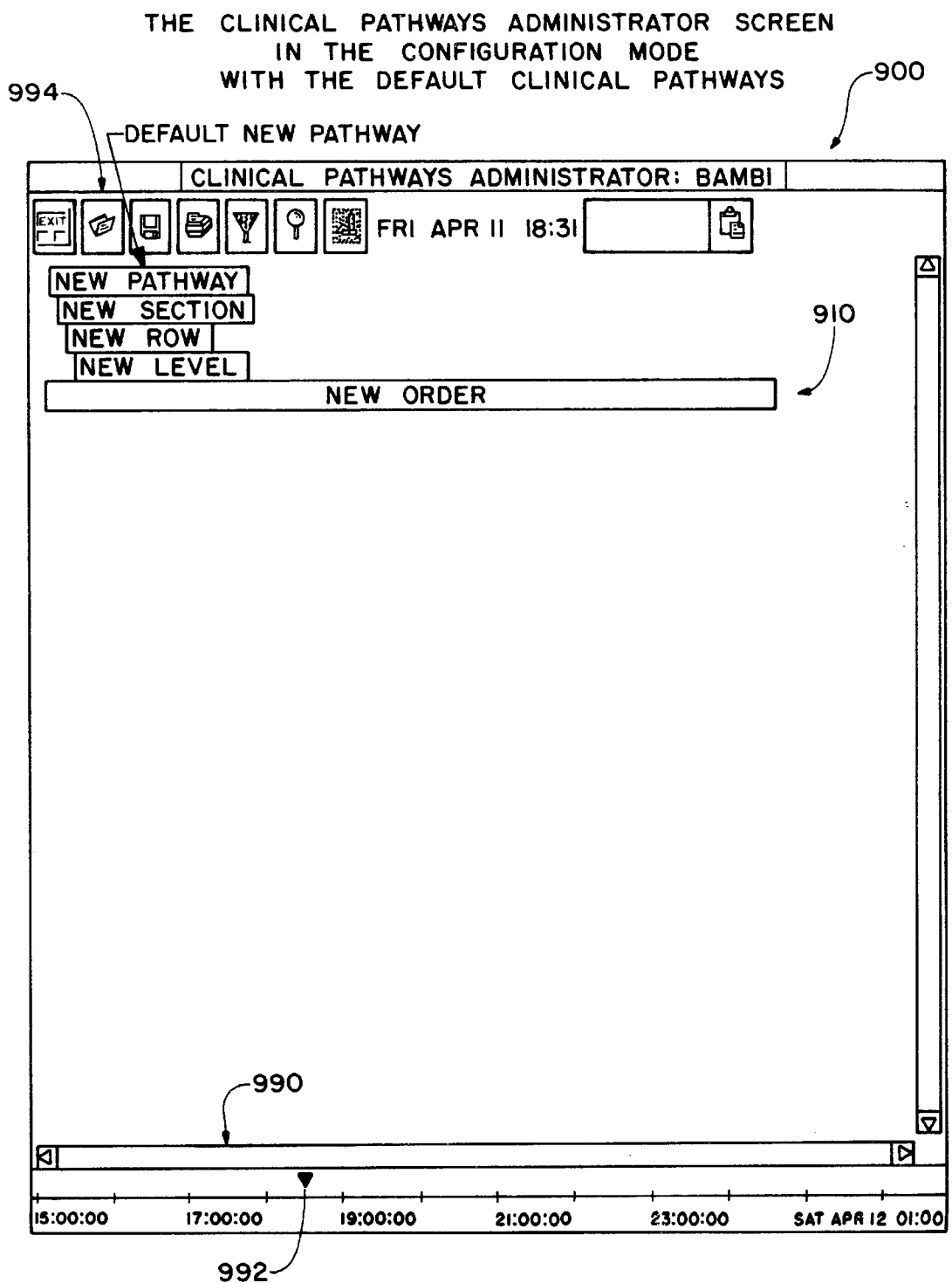
FIG. 11 is a clinical pathways administrator screen in a configuration mode with a default pathway.

Referring now to FIG. 11, there is shown a clinical pathways administration screen 900, illustrating the clinical pathways administration screen in the configuration mode with the default clinical pathway. The screen 900 is created on the monitors of the CIS system.

The screen 900 is a clinical pathway 910, and a time line generally indicated at 990. A downwardly pointing arrow indicates the current time.

A new Clinical Pathway can be created or configured by developing a pathway from scratch; or by copying an existing pathway and modifying it as needed.

To change to the Configuration Mode to modify existing templates or create a new one, the following steps are performed. Select the Clinical Pathway Administrator Screen 900 is selected. The "Configuration Mode" icon is mouse selected by pointing and clicking. A User Verification window then appears. An identification code can then be entered, and then an Enter key (not shown) is pressed. The "Configuration Mode" indicator (not shown) then appears in the middle, center of the screen.

To create a new clinical pathway, the following steps are performed.

The "Open" icon is mouse selected by pointing and clicking. The Current Pathways window then appears. The "New Pathways" choice is then mouse selected by pointing and clicking. The "OK" button is then mouse selected. The pathway level box appears on the screen with the title "New Pathway."

When creating a new clinical pathway, the pathway is configured as follows:

| Action | Function |
| --- | --- |
| Edit the label of the Clinical Pathway | Edit |
| Create the necessary Section Levels | Copy |
| Edit the labels for the Section Levels | Edit |
| Create the necessary row Levels | Copy |
| Edit the labels for the Row Levels | Edit |
| Create the necessary Step Levels | Copy |
| Edit the labels for the Step Levels | Edit |
| Assign the outcome for each level | Outcome |
| Assign the weight for each level | Edit |
| Create orders | New Order |
| Set the Start and Stop Times | Dragging the Level Boxes |

Once the Start and Stop times are set, the Step is completed, and the order level is commenced.

To assign the Outcome for a Step Level, the following steps are performed. The cursor is moved to the Step level. The right moue button is depressed and held. The Edit option is then mouse selected to cause the Edit window to appear.

The Outcome is then entered in the "Outcome" field. The "OK" button is then mouse selected.

To exit from the Configuration Mode, the "Configuration Mode" icon is mouse selected. The "Configuration Mode" indicator then no longer appears in the tool bar 994.

Annotation of objects, and variance analysis is disclosed in Appendix "A."

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A method of facilitating the management of patient care, the method implementing clinical pathway flowsheets on a computer system, comprising:

storing clinical pathway templates, said template being a pre-defined patient care path;

assigning a template to a given patient under treatment;

tailoring the predefined patient care path of the assigned template for the requirements of the given patient;

said tailoring including entering into the computer system order information specific to the given patient relating to the pre-defined patient care path;

said tailoring also including automatically creating an updated clinical pathway flowsheet for the given patient reflecting the tailoring of the assigned template by automatically transferring said entered information to the flowsheet, the updated flowsheet for indicating the progression of patient care for the given patient;

displaying the updated clinical pathway flowsheet at a computer display station wherein the clinical pathway flowsheet indicates a progression of time including the progression of patient care for the given patient;

entering subsequently change information into the computer system relating to the patient care pathway flowsheet provided for the given patient, the change information indicative of a change in the care for the given patient;

recording automatically variance information for the clinical pathway flowsheet for the given patient responsive to the entered change information to inform the user of changes in future patient care for the given patient; and developing a modified, optimized pre-defined care path in accordance with the variance information of the given patient and variance information obtained from a plurality of other clinical pathway patients utilizing the pre-defined care path of the template assigned to the given patient.

2. A method according to claim 1, further including collecting variances from patient care paths for a plurality of patients, including the variance for the given patient, so that the pre-defined patient care path templates can be modified with patient treatment experience.

3. A method according to claim 2, further including modifying said templates in accordance with the collected variances.

4. A method according to claim 1, further including configuring said templates in levels of objects.

5. A method according to claim 4, further including arranging said levels in a hierarchy of a sequence of objects including at least one of the following objects including a clinical pathway, a section, a row, a level and an order.

6. A method according to claim 5, further including configuring individual orders.

7. A method according to claim 5, further including grouping orders into levels.

8. A method according to claim 5, further including grouping orders into rows.

9. A method according to claim 5, further including grouping rows into sections.

10. A method according to claim 5, further including grouping sections into a pathway.

11. A system operating on a computer for facilitating the management of patient care and displaying clinical pathway flowsheets, comprising:

means for storing clinical pathway templates, said template being a pre-defined patient care path;

means for assigning a template to a given patient under treatment;

means for tailoring the pre-defined patient care path of the assigned template for the requirements of the given patient;

said means for tailoring including means for entering into the computer system order information specific to the given patient relating to the pre-defined patient care path;

said means for tailoring also including means for automatically creating an updated clinical pathway flowsheet for the given patient reflecting the tailoring of the assigned template by automatically transferring said entered information to the flowsheet, the updated flowsheet for indicating the progression of patient care for the given patient;

means for displaying the updated clinical pathway flowsheet at a computer display station wherein the clinical pathway flowsheet indicates a progression of time including the progression of patient care for the given patient;

means for entering subsequently change information into the computer relating to the patient care pathway flowsheet provided for the given patient, the change information indicative of a change in the care for the given patient;

means for recording automatically variance information for the clinical pathway flowsheet for the given patient responsive to the entered change information to inform the user of changes in future patient care for the given patient; and means for developing a modified, optimized pre-defined care path in accordance with the variance information of the given patient and variance information obtained from a plurality of other clinical pathway patients utilizing the pre-defined care path of the template assigned to the given patient.

12. A system according to claim 11 further including means for collecting variances from the patient care paths for a plurality of patients, including the variance for the given patient, so that the pre-defined patient care path template can be modified with patient treatment experience.

13. A system according to claim 12, further including means for modifying said templates in accordance with the collected variances.

14. A system according to claim 11, further including means for configuring said templates in levels of objects.

15. A system according to claim 14, further including means for arranging said levels in a hierarchy of a sequence of objects including at least one of the following objects including a clinical pathway, a section, a row, a level and an order.

16. A system according to claim 15, further including means for configuring individual orders.

17. A system according to claim 15, further including means for grouping orders into levels.

18. A system according to claim 15, further including means for grouping levels into rows.

19. A system according to claim 15, further including means for grouping rows into sections.

20. A method of facilitating patient care paths, the method implemented on a computer system, comprising:

entering order information for a given critical care flowsheet;

tailoring the critical care flowsheet by automatically transferring the entered order information to the given flowsheet for each of a plurality of given patients, each tailored critical care flowsheet being indicative of a patient care path for a single given patient;

entering change information into said given flowsheet;

generating automatically a variance responsive to the entered change;

collecting patient care path variances from each of the plurality of given patients; and optimizing delivery of care to each of a plurality of given patients by editing critical care pathway flowsheets for each given patient responsive to the collected variances collected from each respective given patient.

21. A method of facilitating the management of patient care using a computer system, comprising:

storing clinical pathway templates, said templates providing a pre-defined patient care path flowsheet;

assigning a template to a given patient under treatment;

entering order information specific to the given patient into the computer system;

automatically tailoring the assigned template for the requirements of the given patient responsive to the entered information;

said tailoring including generating a critical care flowsheet by transferring the entered information to the flowsheet for the given patient;

displaying the critical care flowsheet for the given patient, the critical care flowsheet showing future patient management information;

subsequently entering a variance into the generated flowsheet;

collecting variances from the critical care flowsheet for the given patient;

collecting variances from a plurality of critical care flowsheets generated from the template so that the pre-defined patient care path templates can be modified with patient treatment experience; and optimizing the pre-defined patient care path templates by modifying said templates in accordance with the collected variances for the templates.

* * * * *